United States Patent
Tajima

[11] Patent Number: 6,143,250
[45] Date of Patent: Nov. 7, 2000

[54] MULTI-VESSEL CONTAINER FOR TESTING FLUIDS

[75] Inventor: Hideji Tajima, Tokyo, Japan

[73] Assignee: Precision System Science Co., Ltd., Tokyo, Japan

[21] Appl. No.: 09/011,263

[22] PCT Filed: Jul. 31, 1996

[86] PCT No.: PCT/JP96/02158

§ 371 Date: Jan. 30, 1998

§ 102(e) Date: Jan. 30, 1998

[87] PCT Pub. No.: WO97/05492

PCT Pub. Date: Feb. 13, 1997

[30] Foreign Application Priority Data

Jul. 31, 1995 [JP] Japan .................................. 7-213051

[51] Int. Cl.[7] ........................................................ B01L 3/00
[52] U.S. Cl. .................. 422/102; 435/288.4; 435/305.3; 356/246; 250/328; 220/23.2; 220/23.4
[58] Field of Search ..................... 422/102, 104, 422/101, 65; 435/305.2, 305.3, 288.4; 356/246; 250/328; 73/864.91; 220/23.2, 23.4, 23.8

[56] References Cited

U.S. PATENT DOCUMENTS

| | | | |
|---|---|---|---|
| 4,146,365 | 3/1979 | Kay et al. | 422/57 |
| 4,466,740 | 8/1984 | Kano et al. | 356/246 |
| 4,720,374 | 1/1988 | Ramachandran | 422/310 |
| 4,877,659 | 10/1989 | Vince | 428/34.1 |
| 5,110,556 | 5/1992 | Lyman et al. | 422/101 |
| 5,225,680 | 7/1993 | Yrjonen et al. | 250/362 |
| 5,294,795 | 3/1994 | Lehtinen et al. | 250/328 |
| 5,424,213 | 6/1995 | Mougin | 436/63 |
| 5,578,490 | 11/1996 | Martinez Ubeira | 435/305.2 |
| 5,789,251 | 8/1998 | Astle | 422/102 |

FOREIGN PATENT DOCUMENTS

| | | |
|---|---|---|
| 50-140182 | 11/1975 | Japan . |
| 55-157751 | 11/1980 | Japan . |
| 56-1352 | 1/1981 | Japan . |
| 58-193253 | 12/1983 | Japan . |
| 59-132335 | 7/1984 | Japan . |
| 60-169572 | 11/1985 | Japan . |
| 61-161744 | 10/1986 | Japan . |
| 62-119460 | 5/1987 | Japan . |
| 64-84148 | 3/1989 | Japan . |
| 1-212356 | 8/1989 | Japan . |
| 3-92761 | 4/1991 | Japan . |
| 3-284697 | 12/1991 | Japan . |
| 4-218775 | 8/1992 | Japan . |
| 4-228100 | 8/1992 | Japan . |

*Primary Examiner*—William H. Beisner
*Attorney, Agent, or Firm*—McDermott, Will & Emery

[57] ABSTRACT

A multiple vessel container for testing fluids comprises a gap part formed to have a width smaller than the caliber of a front end portion of a liquid sucking/discharging line. The gap part has a shape capable of aspirating and discharging all liquid through the front end portion of the line, even when the front end portion is in contact with the inside bottom of the container. The container is formed such that, upon fluid discharging, reaction between a sample and a reagent can be made uniform by discharging and diffusing aspirated liquid.

29 Claims, 10 Drawing Sheets

MULTI-VESSEL CONTAINER FOR TESTING FLUIDS

TITLE OF THE INVENTION

1. Field of the Invention

The present invention relates to a container which is suitable for an analysis inspection which requires a high quantitative accuracy. More particularly the present invention relates to the container by which all of the quantity of a specimen in the container can be substantially completely aspirated with being disposed a front end portion of a pipette tip in contact with a surface of the inside bottom of the container. Moreover, the present invention relates to the container which can largely enhance an efficiency of agitating by uniforming a diffusion of the specimen on the occasion of discharging it.

2. Background of the Invention

In order to maintain a precision of an analysis in a high level, as is well-known, a quantitative precision by a pipette device must be exactly maintained. In case of a conventional container, an inside bottom part of the container is formed so as to have a plane surface or a vertical sectional shape being semicircle or substantially U-like. Therefore, aspirating or discharging a sample and/or a reagent can not be executed in a state that a front end part of a pipette tip remains to be disposed in contact with the inside bottom part of the container. As a result, aspirating or discharging a sample and a reagent can be executed in a situation that the front end part of the pipette tip is kept to be lifted from the inside bottom part of the container slightly. Consequently, a small amount of samples and reagents always remains behind the container. In order to compensate this remaining amount, more amount than the actually necessary amount of aspirating needs be aspirated and/or discharged by the pipette tip. Thus, it is inevitable that samples or reagents being not aspirated remain behind the container. As a result, it has a problem that a high quantitative analysis can not be executed.

A conventional means to solve such a problem is shown in FIG. 16 for example. A front end part 2 of a pipette tip 1 is cut diagonally in order to be able to aspirate and discharge a sample S in a state that the front end part 2 of the pipette tip 1 is disposed in contact with an inside bottom part 4 of a container 3. Also, as shown in FIG. 18, another conventional means in which has one or more caves 5 are mounted in the front end part of the pipette tip 1, is proposed. It is designed so that an opening of the pipette tip 1 can not be blockaded by the contact with the inside bottom part 4 of the container 3.

But, even if the front end part 2 of the pipette tip 1 is cut diagonally, the liquid below a level W in FIG. 16 slightly lower than an upper rim of the opening of the front end part which is cut diagonally, can not be completely aspirated. As shown in FIG. 17, when the aspirated samples and/or reagents are discharged in the container 3, those in the one side of the container 3 are agitated by the pressure of discharging. But, the other side of container 3 which does not face the above-mentioned opening cut diagonally, is not directly affected by the pressure of discharging. Therefore, the conventional means has a problem that the agitating efficiency on the opposite side of the opening is low and it is difficult to get a uniform agitating effect, i.e. a uniform state of reaction. Also, it has a problem that manufacture of the pipette tip is not easier and a cost of manufacture increases.

In the same way, the conventional means which is bored by caves 5 in the front end part of the pipette tip 1, cannot aspirate a liquid S below the position where the caves 5 are bored, too. Also, when the aspirated liquid is discharged, the liquid is discharged only in the direction of the opening of the caves 5. Therefore, the conventional means has the problem that it is difficult to get a uniform agitating effect. Moreover, as the manufacturing step to bore one or more caves 5 is necessary, the conventional means has a problem that the manufacture of pipette tip 1 is complicated and a manufacture cost increases.

When liquid is aspirated and discharged in a state that the front end part of the pipette tip is kept to be lifted from the surface of the bottom part of the container, samples or reagents are tend to stick to the outside surface of the pipette tip. Therefore, the conventional means has a problem that a concentration of a sample is changed by samples or reagents being stuck and has a problem that the conventional means is difficult to get high precision results.

The present invention has been accomplished under these circumstances and has the following objects.

It is a first object of the present invention to provide a container which can solve the above problems of the conventional arts by improvement.

It is a second object of the present invention to provide a container which enables the pipette means to execute a reliable step of dispensing and/or agitating by constituting so as to be able to aspirate and/or discharge in a predetermined quantity without blockading a front end part of a liquid sucking/discharging line, on the occasion of the aspirating and/or discharging samples and/or reagents in the container.

It is a third object of the present invention to provide a container which can realize a high precision inspection of all of the quantity by being able to aspirate all of the quantity in the container, and to treat all of the quantity as being fixed without necessity of the surplus of the samples and/or reagents.

It is a fourth object of the present invention to provide a container which can realize reducing a necessary space by accumulating vessels mounted in the container in a high density and moreover by providing the optimal containers for each process, and can realize the efficient process by reducing a transferring distance of the contents of the container, by a quick and prompt operation, and by saving energy.

It is a fifth object of the present invention to provide a container which has a simple structure, and is easy and inexpensive to manufacture by accumulating vessels in a high density.

It is a sixth object of the present invention to provide a container which can realize a prompt and efficient treatment by providing vessels having various capacity for treating, measuring and holding pipette tip, being necessary to the series of the process within a container.

It is a seventh object of the present invention to provide a container which can be so reliable as preventing from cross-contamination surely.

It is an eighth object of the present invention to provide a container which is suitable to attempt to automate a series of process and to exclude the participation of the operation of human being from beginning to end as much as possible.

It is a ninth object of the present invention to provide a container which can reduce a mechanical driving movement being necessary for the process from beginning to end and can realize such a container that the number of the moving parts for the process are reduced.

THE SUMMARY OF INVENTION

To achieve these objects, the container according to the first aspect of the present invention comprises a gap part formed near a center of an inside bottom part of the container to have a smaller width than a caliber of a front end portion of a liquid sucking/discharging line adapted to be inserted in the container and pulled out of the container, and uniformly falling slope extending from an inside wall of the container toward a border of the gap part, wherein the gap part is formed to have a shape being capable of aspirating and discharging all of the quantity of liquid through the front end portion even in a state that the front end portion is disposed in contact with the inside bottom part.

Thus, the reliable dispensing and/or agitating step by a pipette device can be realized by constituting so as to be able to aspirate and/or discharge a predetermined amount without blockading the front end portion of the liquid sucking/discharging line when the samples and/or reagents in container are aspirated and/or discharged. Moreover, as the present invention can aspirate all of the quantity in the container, a surplus of samples or reagents are not necessary to compensate the remaining amount. As the present invention can treat all of the quantity as being a fixed, the present invention can realize a high precision inspection of all of the quantity. Furthermore, the container can be inexpensively provided because of the simple structure.

A second aspect of the present invention is that, in the first aspect, the gap part comprises a ditch or ditches having a longer size than the caliber of the front end portion of the liquid sucking/discharging line, and being formed to be substantially concave in a vertical section. Though the depth of the ditch or ditches is not restricted to a particular size, it is preferable that the depth is determined to be so shallow as to achieve aspirating all of the quantity. The present aspect of the invention can be more effective than the first aspect of the invention in regard to the uniforomity of agitating.

A third aspect of the present invention is that, in the second aspect, the plural ditches are arranged so as to be radiated. The "radiated" arrangement includes asterisk, cross and three-forked road arrangement et al.

A fourth aspect of the present invention is that, in the first aspect, the gap part is formed so as to have plural concavities or convexities having a smaller size than the caliber of the front end portion of the liquid sucking/discharging line.

A fifth aspect of the present invention is that, in the first to fourth aspect, the gap part is formed so as to have a falling slope extending towards the center of the inside bottom part of a main body of the container. By this aspect of the invention, substantially all of the quantity in container can be aspirated surely.

A sixth aspect of the present invention is that, in the first to fifth aspect, plural vessels for storing liquid and so on are arranged along a line or lines so as to form a cartridge container or a microplate.

This aspect of the invention can realize narrowing a necessary space by accumulating the vessels in a high density and can realize the efficient treatment by shortening a transferring distance of the contents in vessels, by a quick and prompt operation, and by saving energy. Furthermore, a container can be provided in a low price with being a simple structure by accumulating vessels in a high density. As the vessel for measuring light and so on are accumulated in a cartridge container or a microplate, the process from beginning to end can be executed by only one container, and the process can efficiently and promptly be executed by reducing the necessity of the mechanical driving movement.

A seventh aspect of the present invention is that, in the sixth aspect, each vessel is formed to be elliptic in a horizontal section. As the container of this aspect of the invention is formed to be substantially elliptic, the flow of liquid becomes irregular when pipette tip discharges liquid, and the agitating efficiency can be improved by this aspect of the invention.

In this invention, a container may be comprised of a single vessel formed so as to be substantially concave in a vertical section. Or, a container may be comprised of a cartridge container or a microplate, in the main body of which plural vessels are arranged in a straight line or lines. It is preferable that a horizontal section of each vessel for storing liquid is formed so as to be elliptic.

An eighth aspect of the present invention is that, in the sixth or seventh aspect, vessels have various shapes or various capacities determined by a content of process. As the container can be constituted so as to be able to execute necessary treatment by only one container, the process can be completed efficiently and quickly.

A ninth aspect of the present invention is that, in the first to eighth aspect, the container is used for the process of liquid containing magnetic particles. For example, "process for the liquid containing magnetic particles" is chemical luminousness inspection methods or EIA inspection methods such as the CLIA inspection method or the CLEIA inspection method and so on. Naturally, it is possible to use for the other inspection method, an extraction method, and a measurement method, too.

A tenth aspect of the present invention is that, in the first to ninth aspect, in each vessel, an antigen, an antibody, an enzyme or a DNA probe and so on is contained in the solid phase. Here, "is contained in the solid phase" means that an antigen and so on sticks to the inside wall of the container and so on in solid phase by coating and so on.

An eleventh aspect of the present invention is that, in the sixth to tenth aspect, the cartridge container has a base member, and plural vessels arranged along a line or lines in the base member, wherein the plural vessels comprise the necessary number of vessels for treatment, vessels for measuring light being able to couple with an optical measuring apparatus or an optical receiving unit in a light shielded state, or hole parts holding it, vessels accommodating or hole parts holding a pipette tip, tubes for PCR or hole parts holding it, or, vessels being contained in the solid phase or hole parts holding it, according to the process. Thus, the process from beginning to the optical measurement can be completed by only one container. Therefore, the necessity of the mechanical driving movement can be suppressed to the minimum. Also, the process can be promptly, reliably and collectively executed by reducing the distance and the time for the transfer of liquid and so on.

A twelfth aspect of the present invention is that, in the sixth to tenth aspect, the microplate has a base member, and plural vessels arranged in a matrix in the base member, wherein the plural vessels belonging to a group of vessels formed by dividing the matrix row-wise or column-wise comprises the necessary number of vessels for treatment, vessels for measuring light being able to couple with an optical measuring apparatus or an optical receiving unit in a light shielded state, or hole parts holding it, vessels accommodating or hole parts holding a pipette tip, tubes for PCR or hole parts holding it, or, vessels being contained in the solid phase or hole parts holding it, according to the process.

Here, "a tube for PCR (polymerase chain reaction)" is the tube whose shape is adapted to the equipment for the amplification of DNA. By this aspect of the invention, as the same process can be done at the same time by multi-nozzle for dispensing, process can be executed efficiently.

A thirteenth aspect of the present invention is that, in the eleventh or twelfth aspect, the vessel for measuring light comprises a measuring vessel shielded from external light and a hole part holding it dismountably, in the case the base member of the cartridge container or microplate is made of such a transmission material as a transparent material or a translucent material. In this invention, the measuring vessel has a light shielding characteristic can be made as a separate members from the microplate made of a material having a light transmitting characteristic. Consequently, manufacture of them as separate members can be more easier than that as one integral member, and the cost can be reduced.

A fourteenth aspect of the present invention is that, in the eleventh or twelfth aspect, the vessel for measuring light and the base member are formed as a unitary body in the case that the base member of the cartridge container or microplate is made of a light shielding material.

A fifteenth aspect of the present invention is that, in the eleventh to thirteenth aspect, the measuring vessel held in the vessel for measuring light has a coupling means to couple with an optical measuring apparatus or an optical receiving unit in a light shielded state, at the upper end of the meaning vessel, wherein the inside wall of the measuring vessel is formed so as to be of a high reflective rate by applying with white color and so on, and the outside of the measuring vessel is covered by a light shielding material. In order to be of "high reflective rate", it should be applied with white color, be made of white material, be applied with metallic color, or be made of a metal and so on. By this aspect of the invention, external light can be shielded, and light arisen by radiation can surely enter into an optical receiving unit and an optical measuring apparatus, and a reliable measuring can be executed.

A sixteenth aspect of the present invention is that, in the sixth to fifteenth aspect, the microplate or the cartridge container comprises a base member being formed so as to be substantially plate-like, plural vessels being arranged in a matrix or in a line in the base member, a wall-like leg part being projecting downwards at an edge of the base member so as to be lower than the outside bottom of the vessel in order to support the base member. By this aspect of the invention, as microplate and cartridge container can be made without distortion, they can be stably placed on a stage for the pipette device and so on.

A seventeenth aspect of the present invention is that, a container has a microplate or a cartridge container comprising a base member being formed so as to be substantially plate-like, plural vessels arranged in a matrix or in a line in the base member, and a partition or partitions with a fixed height being arranged along parallel to an edge of the base member or a boundary or boundaries separating between groups of vessels. By this aspect of the invention, cross contamination by mixing splashes from the other processing line and so on can be avoided efficiently.

An eighteenth aspect of the present invention is that, in the sixth to seventeenth aspect, one of the vessels is formed so that the structure is adapted to a thermostatic means. For example, when a thermostatic means (for example, a thermostatic tank) which controls the temperature in a tank electrically is used, the tank should be formed so that the vessels can be contained in it.

In comparison with the treatment using only a single vessel, this invention can more efficiently and more completely fascinate the temperature of liquid to be kept at a predetermined temperature by transferring liquid from a liquid storage vessel to a vessel maintained at a predetermined temperature. In comparison with the case using only a single vessel, in which control of raising and lowering the temperature needs be executed by a heating means or transferring a container accompanied by liquid to a heating position, the reaction can more efficiently be executed by this aspect of the invention, and the amplification can be executed more easily and in a shorter time. And as the mechanism for transferring the container needs not be mounted, the structure of the equipment can be simplified. Furthermore, all the process including the control of temperature, can be executed with one continuous operation by this aspect of the invention.

A nineteenth aspect of the present invention is that, in the eighteenth aspect, a lid body having a slit being able to be inserted by the pipette tip, is mounted so as to have a structure being adapted to a thermostatic means. By this aspect of the invention, the evaporation and cross contamination of liquid housed in a container can be efficiently avoided.

A twentieth aspect of the present invention is that, in the sixth to nineteenth aspect, a seal being able to be penetrated by the pipette tip, is attached by a heat deposition or a supersonic deposition to the upper surface of the base member of the cartridge container or the microplate in order to cover the opening of the each vessel.

Here, "a seal being able to be penetrated by a pipette tip" may be not only the tender thin film being easily penetrated, but also the tough one having a hole. The seal may be not only transparent, but also translucent or opaque, and may be made of aluminum foil or polyvinyl-chloride and so on. In order to execute a treatment in a container, the front end portion of the pipette tip needs penetrate the seal and be inserted into the container. By this aspect of the invention, the evaporation of liquid being contained in each vessel and the cross contamination, and the invasion by the miscellaneous germs from outside can be avoided. Therefore, the treatment with high reliability can be efficiently executed.

A twenty-first aspect of the present invention is that, a container has a microplate comprising plural cartridge containers in which the vessels are arranged in a row-wise or column-wise line and a binding part formed so as to be substantially like teeth of a comb having intervals between the cartridge containers being able to be inserted in by the partition and binding the end of each cartridge container, wherein the partitions are arranged so as to be substantially in parallel mutually at a fixed interval on the stage putting the microplate in order to partition the cartridge containers mutually. Here, the size of "a fixed interval" needs be large enough for the cartridge containers of the microplate or each nozzle of multi-nozzle for dispensing to be capable of being separated between partitions one by one, with a certain space. The height of the partition is great enough to prevent from mixing a splash of liquid etc. arisen from pouring etc. Instead of the partition, air curtains may be mounted between cartridge containers in order to prevent from mixing a splash of liquid etc. As each neighboring cartridge container can be separated by a partition, mixture of substances other than target substances between the different cartridge containers (cross-contamination) can be efficiently avoided, and reliable treatment can be executed.

A twenty-second aspect of the present invention is that, in the twenty-first aspect, the binding part is formed so as to have such a strength as each cartridge container to be cut easily. By this aspect of the invention, as the binding part can be cut every cartridge container easily, only the necessary number of the cartridge containers can be cut off from the binding part and be used according to the content of the process, and therefore, cartridge container can be efficiently used without waste and efficiently.

Besides, in the twenty-first aspect of the invention and the present aspect of the invention, if the cartridge containers and the binding part are formed in a unitary body, the manufacture of the container can be simplified and the cost can be reduced. For example, "to be cut easily" can be attained by forming the binding part to be thin.

A twenty-third aspect of the present invention is that, in the sixth to twenty-second aspect, the necessary number of the vessels of the cartridge container according to the process are arranged along a locus of a moving nozzle of the liquid sucking/discharging line, and the necessary number of the vessels of microplate according to each process are arranged in parallel along loci of moving nozzles of the liquid sucking/discharging lines.

A BRIEF DESCRIPTION OF THE DRAWINGS

DESCRIPTION OF THE PREFERRED EMBODIMENTS

Hereinafter, this invention is explained in detail, in conjunction with the embodiment shown in the accompanying drawings. FIGS. 1 to 6 show a container of the first embodiment of the present invention. A container 10 of this embodiment comprises a cartridge container which has a main body 11 of the container made of glass or plastic and so on in a unitary body and a knob 12 formed in the one end of this main body 11. In the above main body 11, plural (nine in the example of the figure) liquid storage vessels 13A–13I, and a hole 13J holding a measuring vessel 14 dismountably.

The above liquid storage vessels 13A to 13I are made of a transparent plastic or glass so as to be capable of seeing through the substances contained in the vessels from outside. Therefore, the inside wall and bottom of the measuring vessel 14 made of a transparent body, which can be dismountably held in the hole 13J holding a vessel, is coated by a light shielding film so as to be capable of measuring a weak chemi-luminescence surely. Namely, the container 10 of this embodiment comprises two parts, one of which is the main body 11 made of a transparent body, and the other of which is the measuring vessel 14.

Naturally, instead of the measuring vessel 14, there are other means which are constituted so as to be able to measure a weak chemi-luminescence surely. One means comprises three parts being assembled to a unitary body, which is constituted so that a light shielding film and a light shielding board is covered in the inside wall and the bottom part. Or, another means is constituted so that a main body 11 itself may be made of an opaque material having a excellent light shielding characteristic or may be formed so as to be a unitary body being applied with such a color with an excellent light shielding characteristic as black or white etc.

Also, in the case that the above measuring vessel 14 is used with being a transparent body, it is preferable that the above hole 13J holding the measuring vessel 14 is formed so as to have a bottom. And it is preferable that the hole 13J may be formed as a unitary body by coating the inside surface of it, may be assembled to a unitary body by covering a light shielding board, or may be formed by applying with such a color with an excellent light shielding characteristic as black or white color etc.

Figure 7:
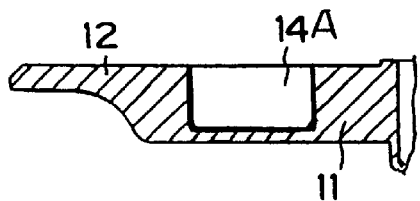
FIG. 7 is a fragmentary expanded vertical sectional view of the cartridge container of the another example of the construction.

Naturally, as shown in FIG. 7, the measuring vessel 14 may be constituted as a measuring hole part 14A which is formed as a unitary body together with a line of liquid storage vessels in the main body 11. In this case, it is preferable that a shielding film is coated on the inside wall and bottom of the measuring hole part 14A. Or, it is preferable that the measuring hole part is assembled to a unitary body with covering a shielding board on the inside wall and bottom of the hole part or making a shielding layer 14B by applying with such a color with an excellent light shielding characteristic as black color or white color and so on.

Thus, the light other than the one arisen from reaction can be shielded, by forming the measuring vessel 14 or the measuring hole part 14A, for example, in the case that the measuring vessel 14 is used for measuring the chemi-luminescence. Naturally, in the case of such a measuring method as that of passing light, that of spectrum, or that of comparing the muddiness etc., the light needs not be shielded. In such a case, the measuring vessel is used with being a transparent body.

Figure 1:
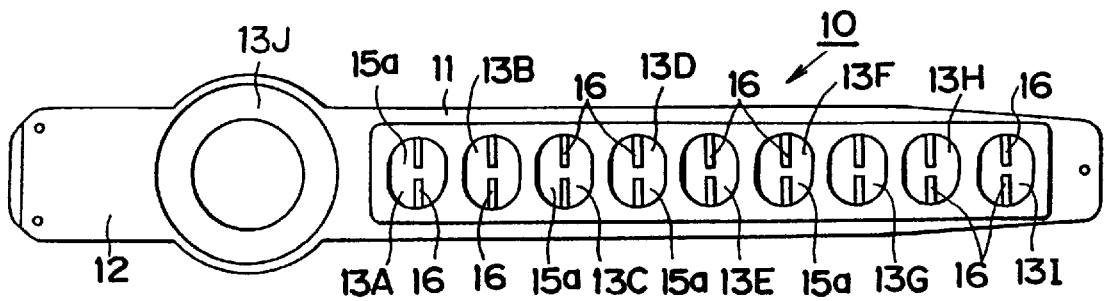
FIG. 1 is a plan view of the cartridge container of the first embodiment of the present invention.
Figure 2:
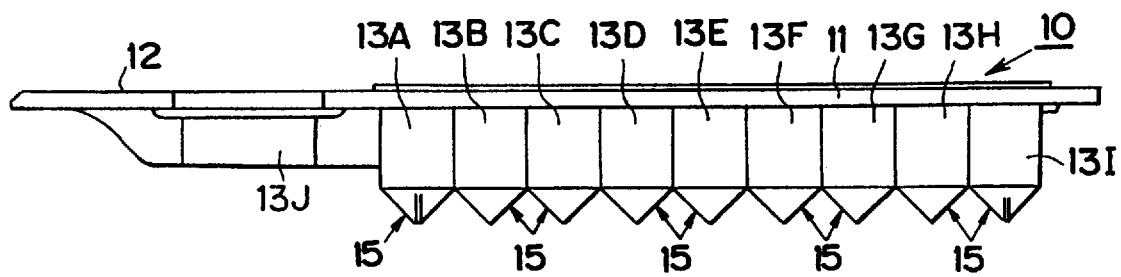
FIG. 2 is an elevational view of the cartridge container shown in FIG. 1.
Figure 3:
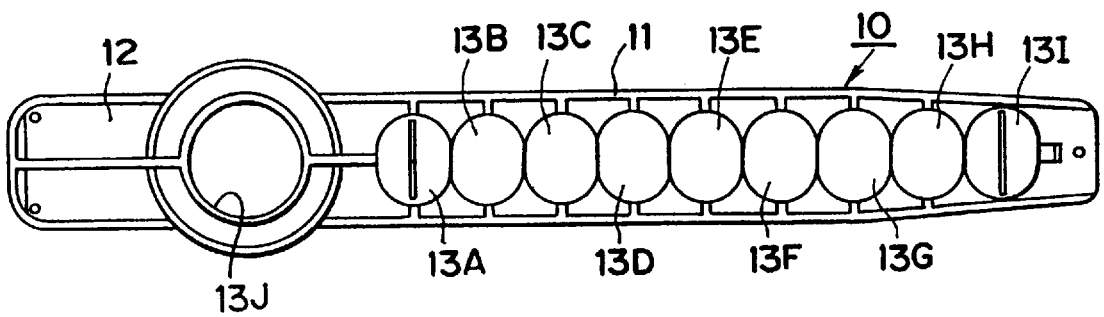
FIG. 3 is a bottom plan view of the cartridge container shown in FIG. 1.
Figure 4:
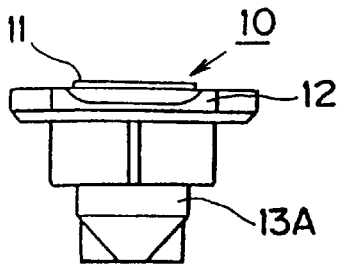
FIG. 4 is a left side view of the cartridge container shown in FIG. 1.
Figure 5:
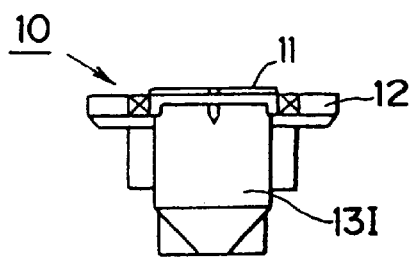
FIG. 5 is a right side view of that cartridge container shown in FIG. 1.
Figure 6:
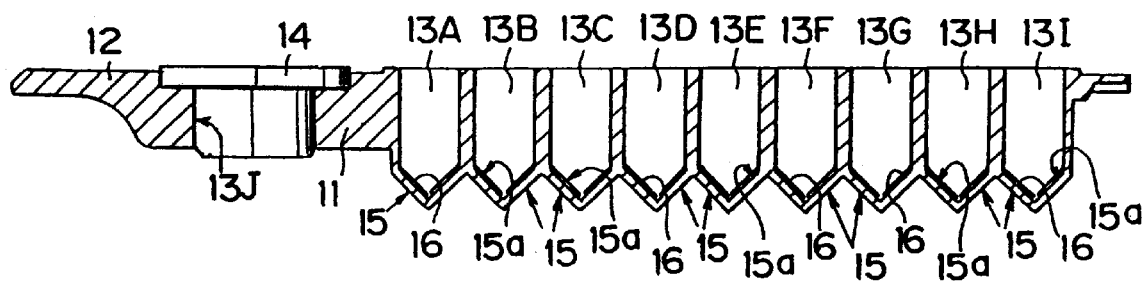
FIG. 6 is a vertical sectional view of that cartridge container shown in FIG. 1.

Besides, the arrangement of the above measuring vessel 14 or the measuring hole part 14A is not limited to the case of this embodiment shown in figures. It is needless to say that the measuring vessel 14 or the measuring hole part 14A can be arranged at suitable positions according to the number of processing steps of measuring items. The above nine liquid storage vessels 13A to 13I are formed so as to be substantially elliptic in a horizontal section, and are formed so as to be substantially V-shape (the illustrated example is the case that the cross angle is 90°) in a vertical section of them. As shown in FIG. 1, in an inside bottom part 15a of each bottom part 15, a ditch 16 whose vertical sectional shape is substantially concave, is mounted along an inclined surface of each inside bottom part 15a.

Figure 8:
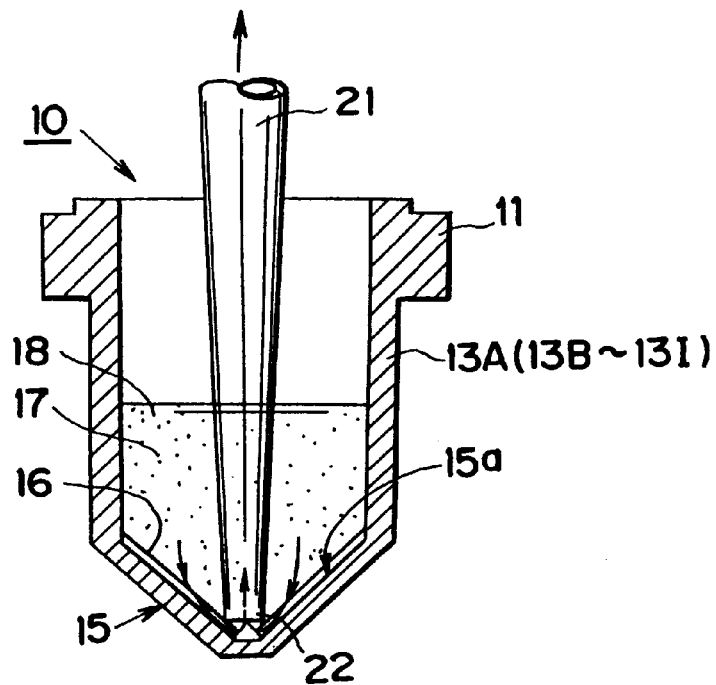
FIG. 8 is an expanded vertical sectional view of the state of aspirating samples and/or reagents in the vessel for liquid of cartridge container shown in FIG. 7.
Figure 9:
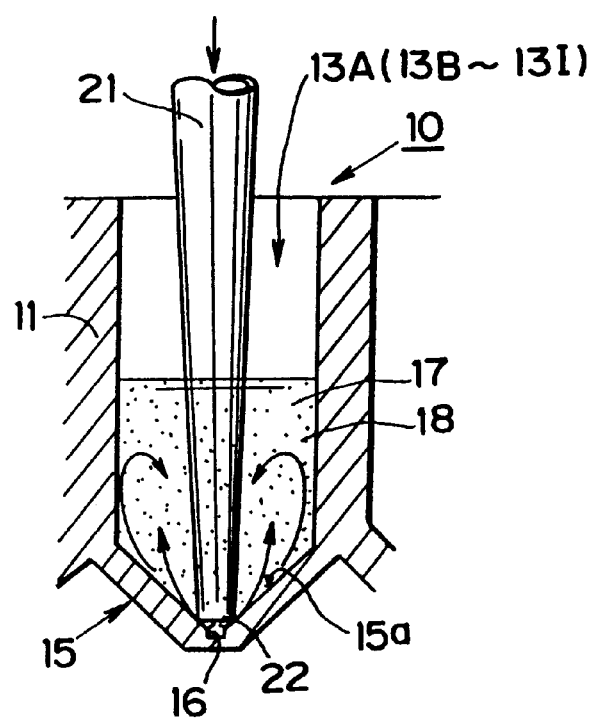
FIG. 9 is an expanded vertical sectional view of the state of discharging samples and/or reagents in FIG. 7.

As is shown FIG. 8 and FIG. 9, the size "d" of the width of this ditch 16 is formed to be smaller than the size "D" of the caliber of a front end portion 22 of the pipette tip 21 (D>d). Also, the length of the ditch 16 is formed to be longer than the caliber of the front end portion 22. Therefore, as is shown in FIG. 8, even if the front end portion 22 of the pipette tip 21 is disposed in contact with a surface of the inside bottom part 15a, all of the quantity of samples and/or reagents contained in vessels 13A to 13I can be aspirated by flow along the ditch 16. Also, a high quantitative accuracy necessary to this kind of equipment can be surely guaranteed by this embodiment. And the waste of the amount of samples and/or reagents can be avoided.

Figure 18:
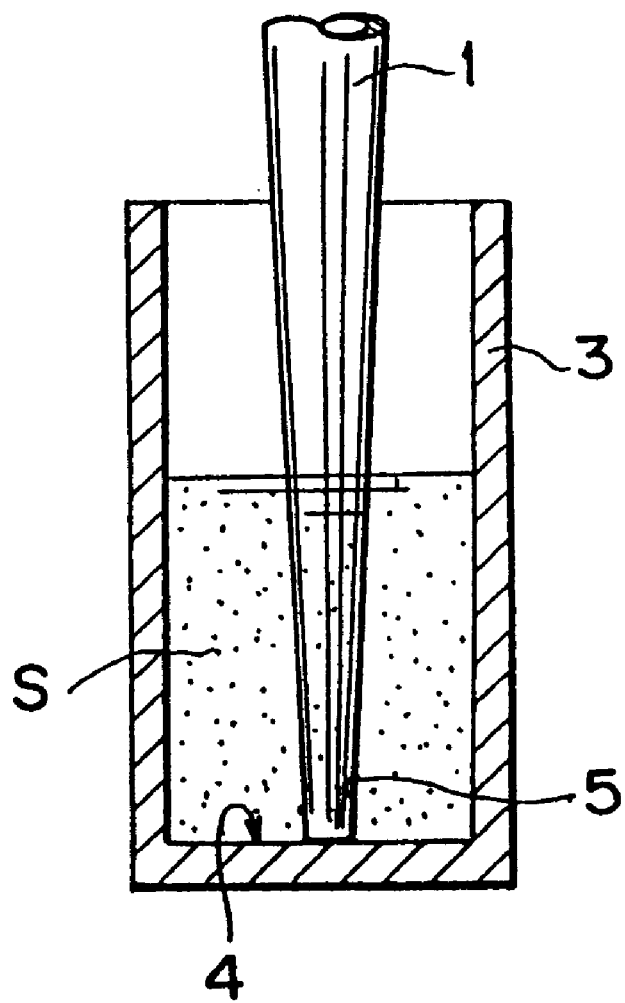
FIG. 18 is a vertical sectional view of the state of aspirating samples or reagents in the other conventional container.

Besides, in this embodiment, samples and/or reagents 18 containing magnetic particles 17 which are used in such an analysis inspection of the chemi-luminescence as a measuring method of CLIA or CLEIA etc. is shown in FIG. 18. But, the samples and/or reagents used in this invention does not limit to the case of this embodiment. For example, this embodiment can be applied to an inspection of EIA which is achieved by providing a vessels to whose inside wall is stuck to, for example by antigen and antibody in the solid phase. It is needless to say that this embodiment is not limited to the stated method given as an example, but can be applied to the other method.

Furthermore, because of the existence of the ditch 16, even if the front end portion 22 of the pipette tip 21 is disposed in contact with the inside bottom part 15a of the liquid storage vessels 13A to 13I as is shown in FIG. 9 on the occasion of discharging the samples and/or reagents to the vessels 13A to 13I, discharged samples and/or reagents flow out through the ditch 16 to within the vessels 13A to 13I in the direction of right and left well-balancedly. Therefore, the flow agitated by discharging of the samples and/or reagents is uniformed, and uniform state of reaction can be obtained by this embodiment.

Besides, the number of the liquid storage vessels 13A to 13I is not limited to this shown embodiment. It is needless to say that the number of the vessels can be varied according to the number of the reaction steps of the measuring items.

Figure 10:
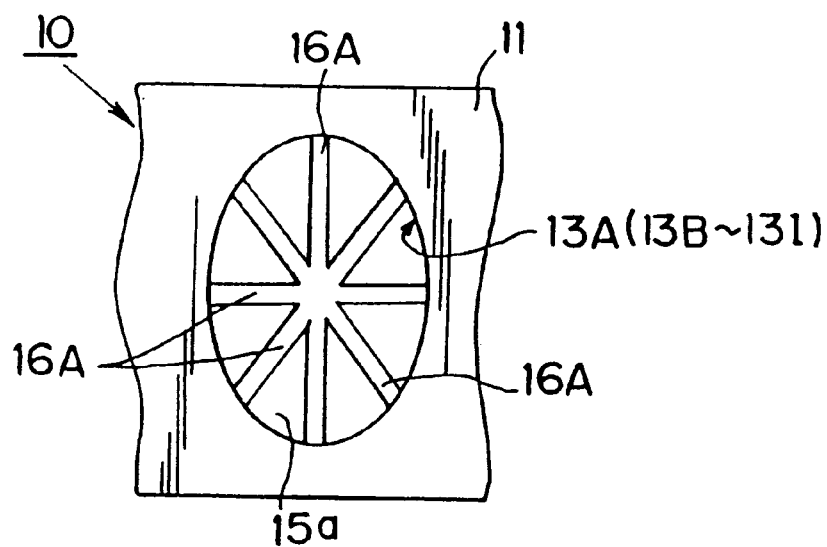
FIG. 10 is an expanded plan view of the vessel for liquid of cartridge container of the second embodiment of the invention.

FIG. 10 shows a plane view of the liquid storage vessels 13 of the container 10 of the second embodiment of this invention. In this embodiment, ditches 16 A, each of the structure is formed to be similar to the ditch 16 of the first embodiment, are arranged so as to be radiated. Thus, all of the quantity of the samples and/or reagents in the liquid storage vessels 13 can be aspirated and/or discharged more promptly and more surely. As the remainder of the structure and the action are similar to that of the first embodiment, the detail explanation is abbreviated here.

Figure 11:
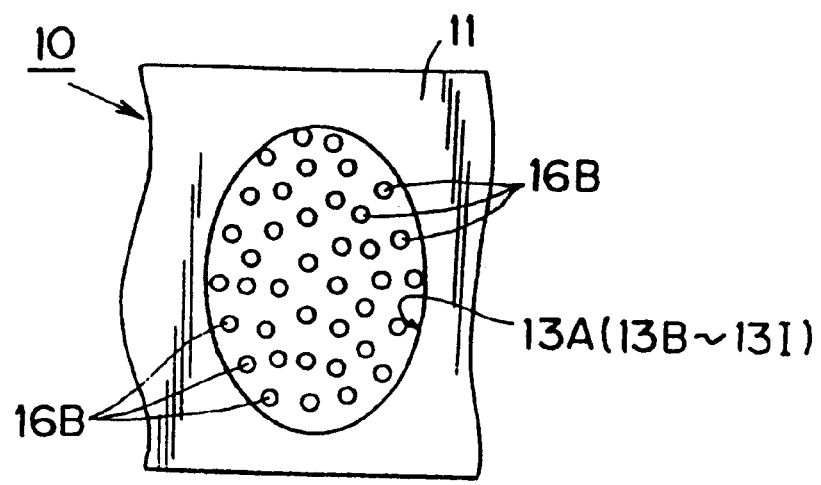
FIG. 11 is an expanded plan view of the vessel for liquid of cartridge container of the third embodiment of the invention.

FIG. 11 shows a plane view of liquid storage vessels 13 of a container 10 of the third embodiment. In this embodiment, instead of ditch 16 or ditches 16A of the first embodiment or the second embodiment, plural concavities or convexities 16b are mounted. And this size of the distance between concavities or convexities is formed to be smaller than that of the caliber of the front end portion of the pipette tip 21, and is formed to be slightly larger than the diameter of the opening of the front end portion in order to discharge and/or aspirate all of the quantity of samples and/or reagents. As the remainder of the structure and the action are similar to that of the first embodiment, the detail explanation is abbreviated here, too.

Figure 12:
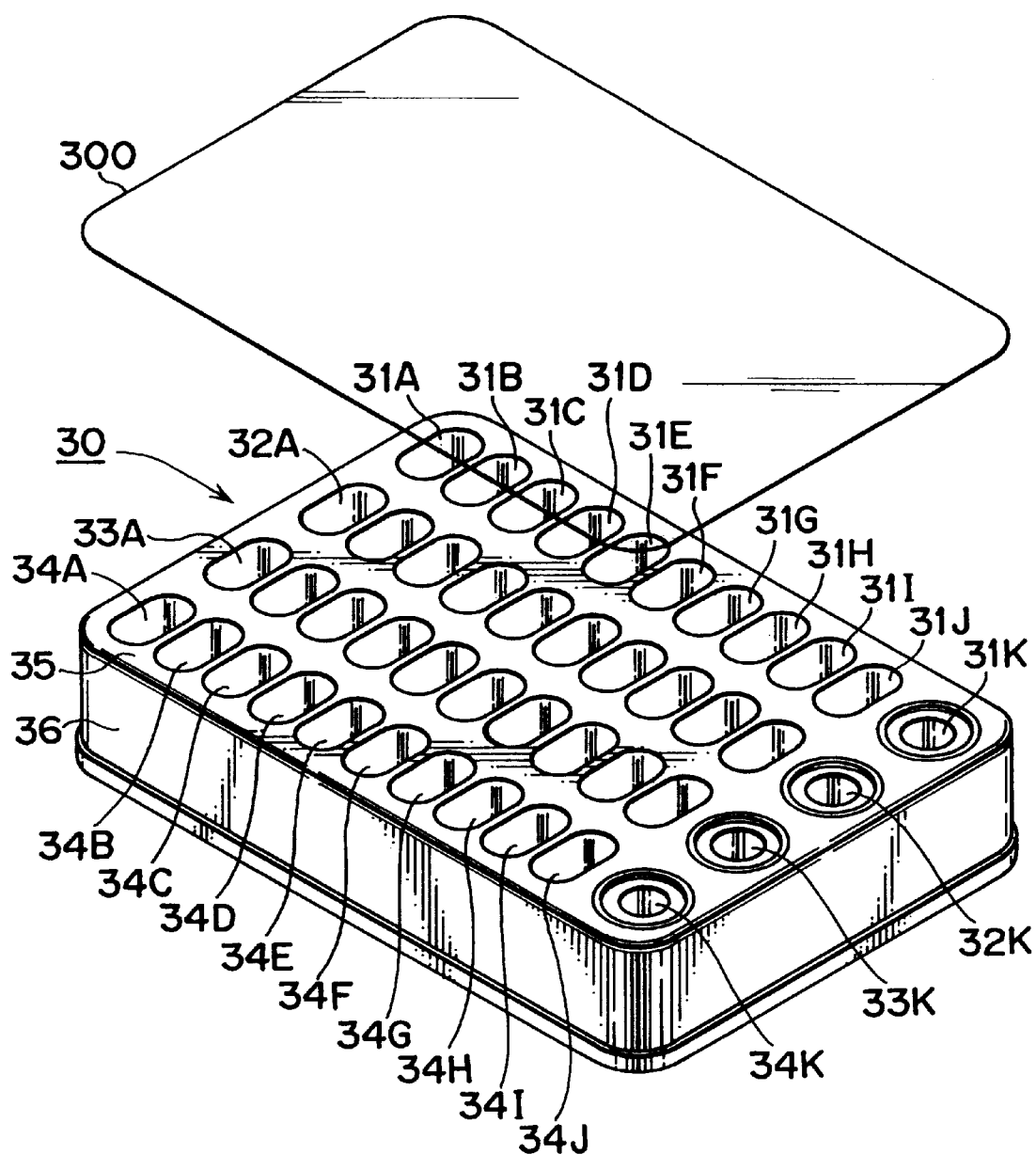
FIG. 12 is a perspective view of the microplate of the forth embodiment of the invention.
Figure 13A:
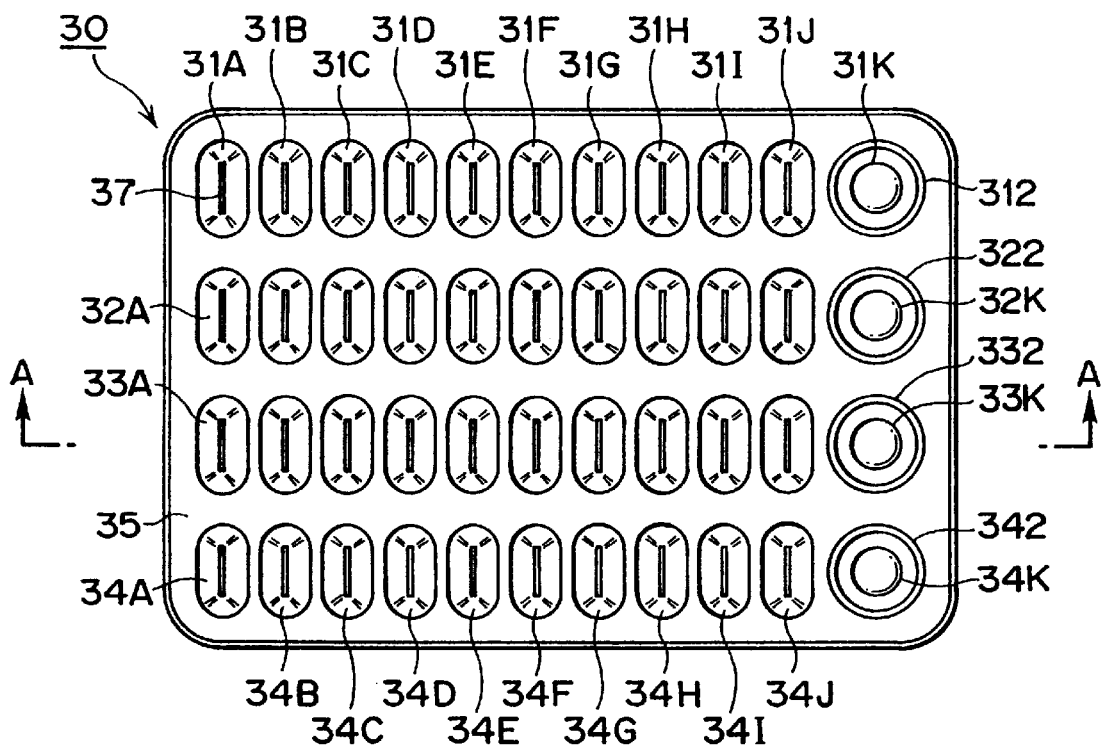
FIG. 13(a) is a plane view of the microplate shown in FIG. 12.
Figure 13B:
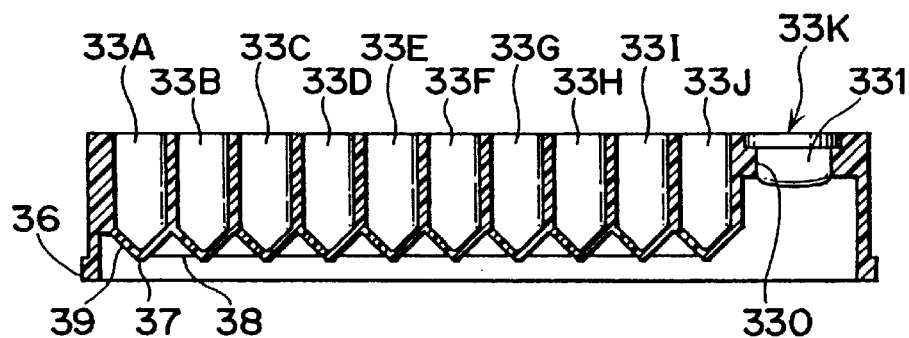
FIG. 13(b) is a vertical sectional view taken in the direction of the arrows along the line A—A of FIG. 13(a).

On the basis of FIG. 12 and FIG. 13, microplate 30 in which the liquid storage vessels are arranged in a matrix, is described as the fourth embodiment of the present invention. Microplate 30 is used for process which is executed by plural liquid sucking/discharging lines stood in parallel. Each line of vessels in the microplate is used, when work of separating, taking out, pipetting, cleaning, condensing, and/or diluting said target high molecular substance and so on or/and works for capturing, extracting, isolating, amplifying, labeling, and/or measuring the substance and so on are executed according to the same timing.

FIG. 12 and FIG. 13 shows that microplate 30 of this embodiment comprises substantially plate-like base member 35 made of a transparent or translucent material, and plural vessels 31A–31K, 32A–32K, 33A–33K, 34A–34K arranged in a matrix-shape in the base member 35. Plural vessels comprise the four groups of vessels 31A–31K, 32A–32K, 33A–33K, 34A–34K which are formed by dividing the matrix into each column (or row). The vessels 31K, 32K, 33K, 34K at the end of each group of the vessels formed by dividing into each column (row) are those for measuring light which can be coupled with an optical measuring apparatus or an optical receiving unit (is not shown in a figure) in a light shielded state.

The vessels 31K, 32K, 33K, 34K comprise hole parts 330 which dismountably hold the measuring vessel 331 which is shielded from an external light and can measure an internal light. The reason for this separate members structure is as follows: The base member 35 itself has not a light shielding characteristic and the measuring vessel 331 needs have a light shielding characteristic. Therefore, the manufacture as separate members is more easier than that as one integral member.

The measuring vessel 331 has the structure that the outer part is made of the black materials having a light shielding characteristic and the inner part is made of the white materials having a light shielding characteristic and an excellent reflection characteristic.

At the upper end of the measuring vessel 331, the coupling portion 332 is mounted which has an annular projection coupling with the optical measuring apparatus or the optical receiving unit in a light shielded state. The annular projection presses against an elastic packing mounted in the optical measuring apparatus or optical receiving unit, and the light is completely shielded.

Thus, the measuring vessel 331 being as separate member from the base member, can be manufactured inexpensively and more easily than the case that the black measuring vessel 331 made of the materials having a light shielding characteristic is mounted in the base member 35 as one integral member.

FIG. 12 shows that the seal 300 which is made of a transparent and thin film which can easily be inserted by the front end portion of the pipette tip, is preferably mounted on the upper surface of the microplate 30 by heat disposition or super-sonic disposition in order to cover each vessel. Thus, the evaporation of liquid contained in vessels beforehand and the invasion of various bacterium from the exterior can be avoided, and the reliable treatment can efficiently be executed.

FIG. 13 shows that the microplate 30 is provided with a wall-like leg part 36 in order to support the base member 35 which is projected downward at the edge of the base member 35 so as to be lower than the outside bottom part 39. Also, ribs 38 for reinforcement are mounted between the neighboring vessels. Consequently, microplate can stably be placed on the stage of the pipette device.

Figure 14A:
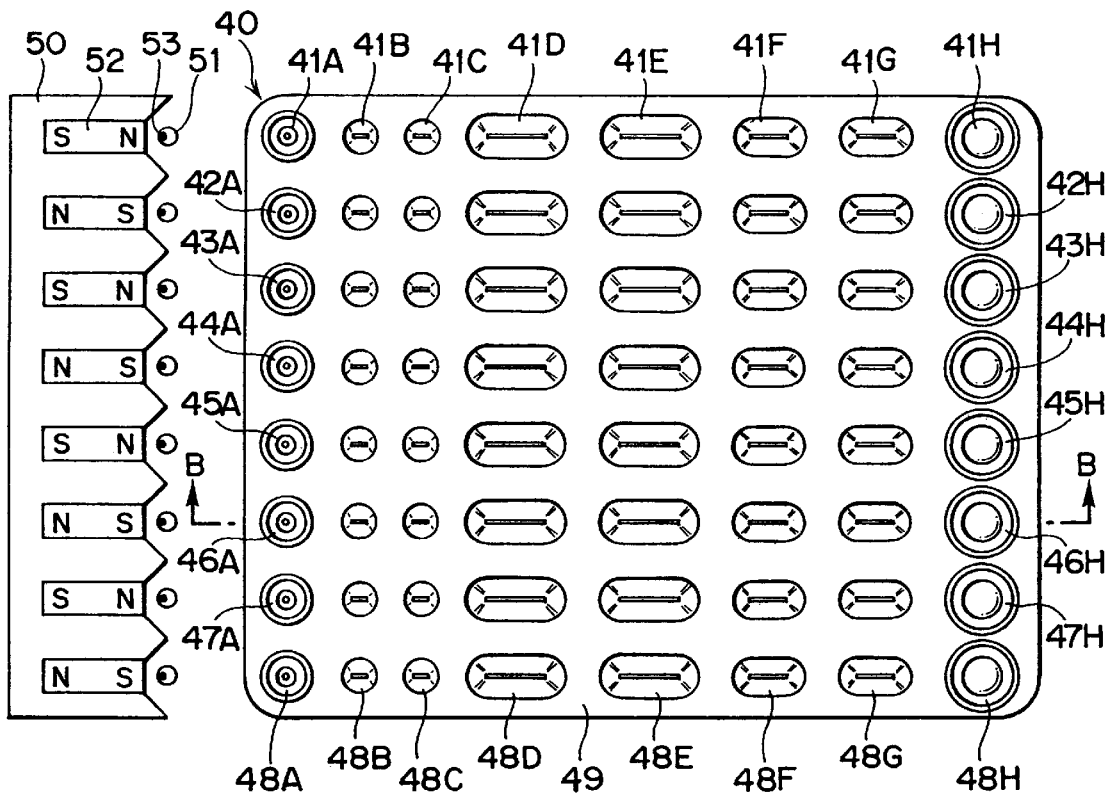
FIG. 14 (a) is a plane view of the microplate of the fifth embodiment of the invention.
FIG. 14(b) is a vertical sectional view taken in the direction of the arrows along the line B—B of FIG. 14(a).
Figure 14B:
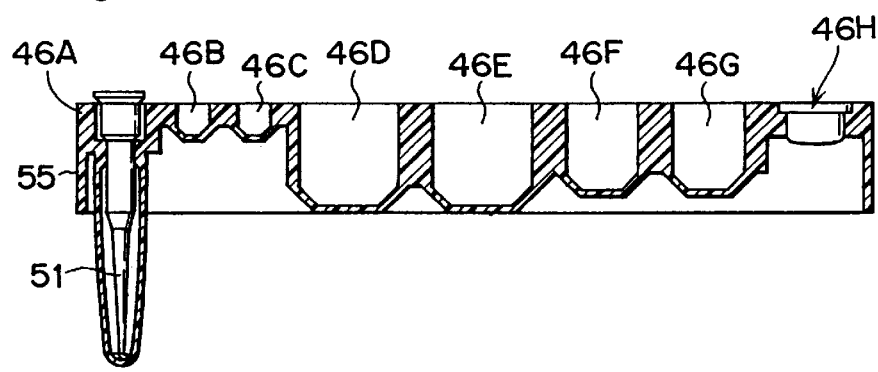

FIG. 14 shows the fifth embodiment of the present invention. The microplate 40 of this embodiment has eight lines of the group of the vessels 41A–41H, . . . 48A–48H. At the end of each group of the vessels, the tip holding vessels 41A–48A are mounted in order to hold the pipette tips 51 being dismounted. At the other end of each group of vessels, measuring vessels 41H–48H are mounted. The vessels 41B–41G, . . . ,48B–48G mounted at the positions except the both ends are formed so as to have various capacities corresponding to the necessary amount of liquid (reagent etc.) according to the treatment.

On the left end of FIG. 14(a), it is shown that eight pipette tips 51 which are equipped with eight nozzles of pipette device executing distribution to the vessels for reaction, eight permanent magnets 52, and transferring body 50 which holds and transfers the eight permanent magnets 52. The permanent magnet 52 is used in order to control a reaction, agitation, separation, cleaning and movement etc. of magnetic particles 53 at the same time, by being simultaneously brought close to or away from a liquid passage which has a middle diameter and joins a reservoir portion having a larger diameter with the front end portion, or by applying a magnetic field to or removing it from the liquid passage. The permanent magnets, 8 in number for example, are disposed in parallel with each other, and in such a manner that the S and N poles alternately occurred. By this structure, the interference of the magnetic field between the neighboring permanent magnets can be avoided, and the stable control can be executed.

In this embodiment, as is shown in FIG. 14, such a structure as a ditch which is substantially concave in a vertical section, is mounted along the inclined surface, is similar to the one that has already been explained by FIG. 1 and so on.

Figure 15A:
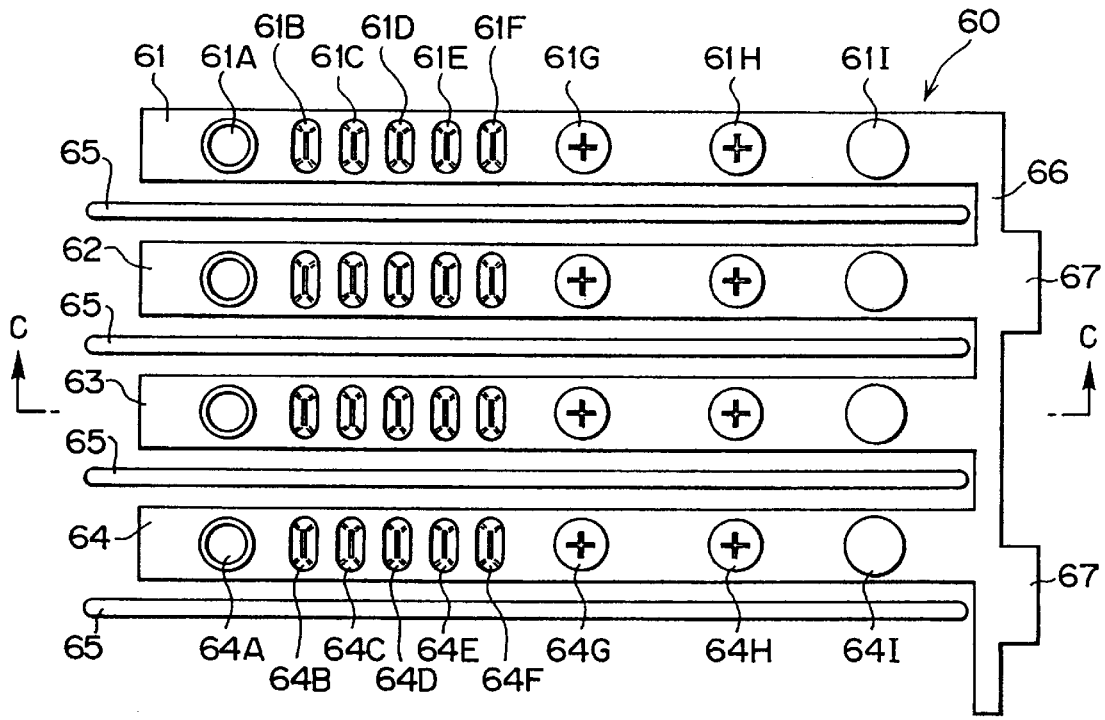
FIG. 15(a) is a plane view of the microplate of the sixth embodiment of the invention.

In succession, on the basis of FIG. 15, the sixth embodiment is described. This embodiment is a container being suitable to the process of the inspection of DNA. As shown in FIG. 15(a), the microplate 60 of this embodiment comprises plural cartridge containers 61, 62, 63, 64 in which vessels are arranged in a line of each column or each row, and the binding part 66 which is formed to be substantially like teeth of a comb, and which binds each end part of cartridge containers arranged at a fixed interval between neighboring cartridge containers. The knob 67 is mounted in the binding part 66 for grasping the microplate 60.

In this embodiment, the cartridge container and binding part and so on are formed in a unitary body by a metal molding. Here, a fixed interval" is determined to be slightly wider than the thickness of the partition 65 arranged on the stage where the microplate 60 is placed in order that the partition 65 can be inserted. When the partitions 65 are inserted into the intervals between the neighboring cartridge containers, each neighboring cartridge container is partitioned with the partition 65.

Figure 15B:
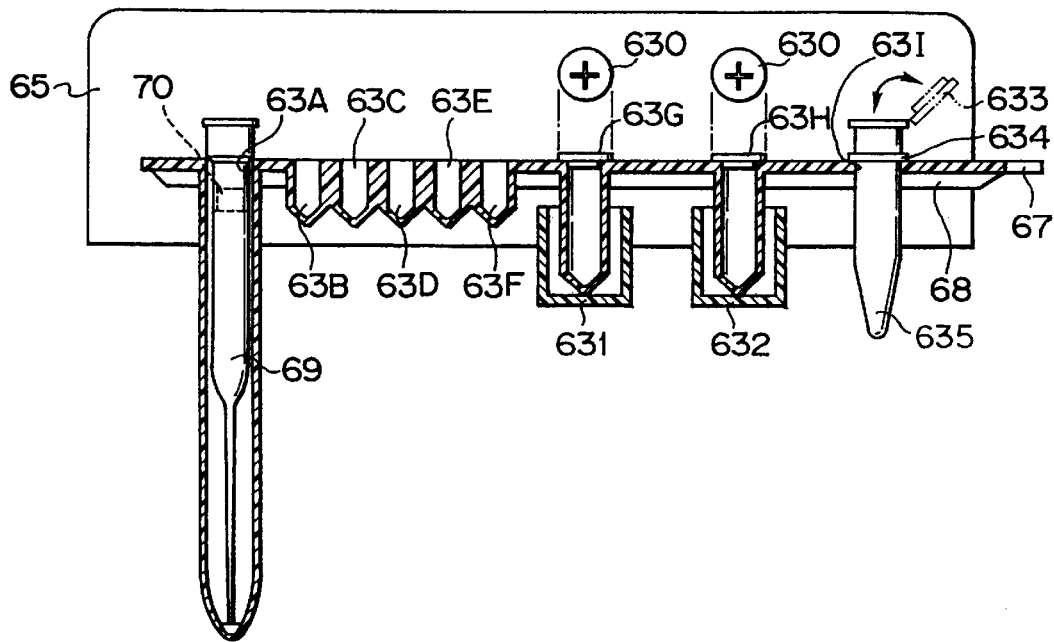
FIG. 15(b) is a vertical sectional view taken in the direction of the arrows along the line C—C of FIG. 15(b).
Figure 16:
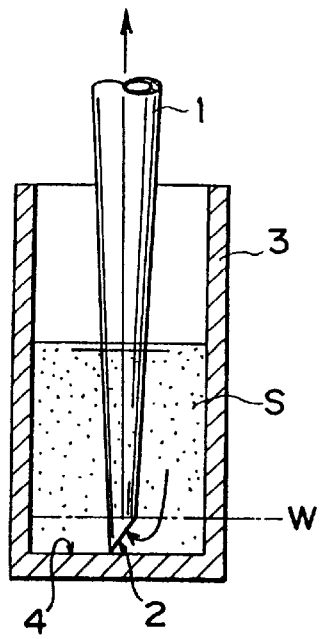
FIG. 16 is a vertical sectional view of the state of aspirating samples or reagents in the conventional container.
Figure 17:
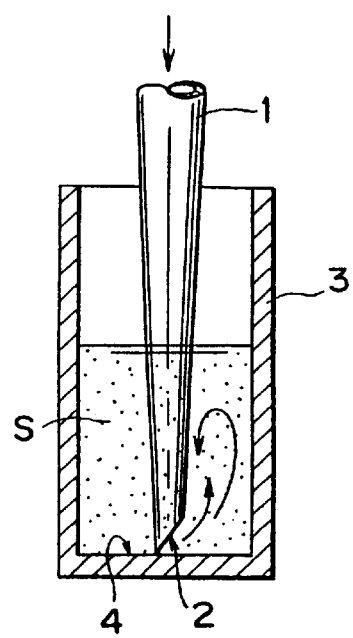
FIG. 17 is a vertical sectional view of the state of discharging samples or reagents in the conventional container.

As shown in FIG. 15(b), in this embodiment, at the one end of each cartridge containers 63 etc., tip holding vessel 63A which holds the pipette tip 69 being dismounted from nozzle, is mounted. At the other end of each cartridge container, the hole part 63I which holds the tubes 635 for PCR that is used for measuring the DNA, is mounted.

In order to prevent from the evaporation of liquid, a lid body 633 can be opened or closed freely, is mounted at the upper end of the tube 635 for PCR. The lid body 633 and the body of the tube are formed so as to be in a unitary body. The tube 635 is supported by the hole part 63I at the flange 634 mounted in the tube 635.

Furthermore, in this embodiment, treating vessels 63B, 63C, 63D, 63E, 63F, 63G, 63H for treating liquid are included. In these vessels, vessels 63G, 63H are mounted so as to be placed at such a position and have such a size, as being able to be contained in a thermostatic tank 631, 632 corresponding to the thermostatic means, and are kept at a predetermined temperature 60° C., 90° C. and so on by this thermostatic tank. The vessels are placed away from the other vessels to some extent in order to give no affection by conduction of the heat. Also, in order to prevent evaporation of liquid during maintaining at a predetermined temperature for a long time, the vessels 63G, 63H are covered by the lid body 630 which is made of elastic body and has a cross-like slit. By this cross-like slit, the front end portion of the pipette tip can intrude into the vessels 61G, 61H, without the lid body being opened.

In order to use the container 60 of this embodiment, the container 60 is put on the stage from above the partitions 65, so that the partitions 65 are stuck out of the intervals of the teeth-of-a-comb-like container 60.

The partitions 65 stands at a fixed interval in parallel, and each cartridge container 61–64 of the microplate 60 is placed in each interval between the partitions 65. In this occasion, as is shown in FIG. 15(b), the vessels 63G, 63H etc. are placed at a predetermined position within a thermostatic tank 631,632. Then, four pipette tips equipped to the four nozzles moves along parallel to the partitions 65, and execute aspirating/discharging and so on at the same time.

Besides, in FIG. 15(b), reference numeral 70 represents a filter. And as shown in FIG. 15(a), in this embodiment, too, at the inside bottom part of vessels 61B–61F and so on, a ditch whose vertical section is substantially concave, is mounted along the inclined surface.

According to this embodiment, each cartridge container is separated by the partition 65. Therefore, cross-contamination by mixing substances except the target substance like DNA etc. can be avoided between processing lines of cartridge containers 61–64. Also, in this embodiment, though the rectangular plate body is disclosed as a partition, an air absorbing device which has an absorbing air opening elongated along lines may be mounted between processing lines, instead of the partition. By this embodiment, a curtain of downward air stream is generated. Consequently the interchange of the air etc. between the neighboring lines, and can prevent from mixing liquid etc. from the other lines can be avoided.

Besides, in the embodiment explained above, the above containers 10 are not only limited to the case that the liquid storage vessels 13A–13I are arranged to be line-like, or are formed to be microplate-like, but also may be arranged to be loop-like or zigzag-like. Or, the container may be formed so as to have a single vessel which is formed to be similar to the above liquid storage vessel. Also, in the above embodiments, the number and the sort of the vessels being mounted in the microplate and the cartridge container are not limited to the above examples. It is needless to say that the number and the sort can be varied as occasion demands.

What is claimed is:

1. A container comprising a gap part formed near a center of an inside bottom part of the container to have a smaller width and a greater length than a caliber of a front end portion of a liquid sucking/discharging line adapted to be inserted in the container and pulled out of the container, and a uniformly falling slope extending from an inside wall of the container toward a border of the gap part, wherein the gap part is formed to have a shape capable of aspirating and discharging all of a quantity of liquid through a front end portion even in a state that the front end portion is disposed in contact with an inside bottom part, wherein a surface of the slope is continuously and smoothly formed from the inside wall of the container to the border of the gap part, in the falling direction, and the surface of the slope and the gap part is free of protrusions or depressions.

2. A container according to claim 1, wherein the gap part comprises a ditch or ditches having a longer size than the caliber of the front end portion of the liquid sucking/discharging line, and being formed to be substantially concave in a vertical section.

3. A container according to claim 2, wherein the plural ditches are arranged so as to be radiated.

4. A container according to claim 1, wherein the gap part is formed so as to have a falling slope extending towards the center of the inside bottom part of a main body of the container.

5. A container comprising plural vessels for storing liquid arranged along a line or lines so as to form a cartridge container or a microplate, wherein each vessel comprises a gap part formed near a center of an inside bottom part thereof with smaller width and greater length than a caliber of a front end portion of a liquid sucking/discharging line adapted to be inserted in the vessel and pulled out of the vessel, and a uniformly falling slope extending from an inside wall of the vessel toward a border of the gap part, wherein the gap part is of a shape capable of aspirating and discharging all of the quantity of liquid through the front end portion even in a state that the front end portion is disposed in contact with the inside bottom part, wherein a surface of the slope is continuously and smoothly formed from the inside wall of the vessel to the border of the gap part in the falling direction, and the surface of the slope and the gap part is free of protrusions or depressions.

6. A container according to claim 5, wherein each vessel is formed to be elliptic in a horizontal section.

7. A container according to claim 5, wherein vessels have various shapes or various capacities determined by a content of process.

8. A container according to claim 5, wherein in each vessel a liquid containing magnetic particles is contained.

9. A container according to claim 5, wherein in each vessel, an antigen, an antibody, an enzyme or a DNA probe is contained in the solid phase.

10. A container according to claim 5, wherein the plural vessels form a microplate or a cartridge container comprising a base member, and the plural vessels are arranged in a matrix, or along a line or lines, respectively, in the base member, wherein the microplate or the cartridge container comprises one or more vessels for measuring light being able to couple with an optical measuring apparatus or an optical receiving unit in a light shielded state, wherein the one or more vessels for measuring light comprise one or more measuring vessels shielded from external light and one or more hole parts for holding the measuring vessels dismountably, and the base member of the cartridge container or microplate is made of a transparent or translucent material.

11. A container according to claim 10, wherein the vessels for measuring light and the base member are formed as a unitary body, and the base member of the cartridge container and the microplate is made of a light shielding material.

12. A container according to claim 10, wherein the vessel for measuring light has a coupling means to couple with an optical measuring apparatus or an optical receiving unit in a light shielded state, at an upper end of the measuring vessel, wherein the inside wall of the measuring vessel is formed so as to be reflective, and the outside of the measuring vessel is covered by a light shielding material.

13. A container according to claim 5, wherein the microplate or cartridge container comprises a base member formed so as to be substantially plate-like, plural vessels being arranged in a matrix or in a line in the base member, a wall-like leg part thereof projecting downwards at an edge of the base member so as to be lower than the outside bottom of the vessel in order to support the base member.

14. A container according to claim 5, wherein the microplate or cartridge container comprises a base member formed so as to be substantially plate-like, the plural vessels thereof arranged in a matrix or line in the base member, and a partition or partitions with a fixed height being arranged parallel to an edge of the base member or a boundary or boundaries separating groups of the vessels belonging to a line or lines of vessels or a cartridge container for bounding only on one side or opposite two sides thereof with a fixed height greater than that of an opening section of each vessel.

15. A container according to claim 14, wherein one or more vessels are contained in thermostatic tanks.

16. A container according to claim 15, wherein a lid body having a slit able to be inserted by a pipette tip, is mounted over the opening of the vessels contained in the thermostatic tanks.

17. A container according to claim 14, wherein a seal able to be penetrated by a pipette tip is attached to an upper surface of the base member of the cartridge container or microplate to cover the opening of each vessel.

18. A container according to claim 5, wherein a thermostatic means is installed in the one of the vessels.

19. A container according to claim 18, wherein a lid body having a slit able to be inserted by the pipette tip, is mounted to the thermostatic means.

20. A container according to claim 5, wherein a seal able to be penetrated by a pipette tip, is attached by heat deposition or supersonic deposition to the upper surface of the base member of the cartridge container or microplate in order to cover the opening of the each vessel.

21. A container according to claim 5, wherein the liquid sucking/discharging line contains a movable nozzle and wherein a necessary number of the vessels of the cartridge container according to a prescribed process are arranged along a locus of movement of the moveable nozzle of the liquid sucking/discharging line, and the necessary number of the vessels of a microplate according to prescribed processes are arranged in parallel along loci of moving nozzles of the liquid sucking/discharging lines.

22. A container according to claim 5, wherein the gap part comprises a ditch or ditches having a greater size than the caliber of the front end portion of the liquid sucking/discharging line, and being substantially concave in a vertical section.

23. A container according to claim 22, wherein the plural ditches are arranged so as to be radiated.

24. A container according to claim 5, wherein the gap part has a falling slope extending towards the center of the inside bottom part of a main body of the container.

25. A container having a microplate comprising plural cartridge containers in which vessels are arranged in a row-wise or column-wise line in a base member thereof and a binding part formed so as to be substantially like teeth of a comb having intervals between the cartridge containers able to be inserted by partitions and fixedly binding only one end of each cartridge container, wherein the partitions are fixedly arranged so as to be substantially in parallel mutually at a fixed interval on the stage where the microplate is put and are projected upward above the opening section of each vessel in order to mutually partition the cartridge containers.

26. A container according to claim 25, wherein the binding part is formed so as to have such a strength that each cartridge container can be cut easily.

27. A container according to claim 25, wherein the liquid sucking/discharging line contains a movable nozzle and wherein a necessary number of vessels of the cartridge container according to a prescribed process are arranged along a locus of movement of the movable nozzle of the liquid sucking/discharging line, and the necessary number of vessels of a microplate according to prescribed processes are arranged in parallel along loci of moving nozzles of the liquid sucking/discharging lines.

28. A container comprising a gap part formed near a center of an inside bottom part of the container to have a smaller width and a greater length than a caliber of a front end portion of a liquid sucking/discharging line adapted to be inserted in the container and pulled out of the container, and a uniformly falling slope extending from an inside wall of the container toward a border of the gap part, wherein the gap part is formed to have a shape capable of aspirating and discharging all of a quantity of liquid containing magnetic particles through a front end portion even in a state that the front end portion is disposed in contact with an inside bottom part, wherein a surface of the slope is continuously and smoothly formed from the inside wall of the container to the border of the gap part, in the falling direction, and the surface of the slope and the gap part is free of protrusions or depressions.

29. A container having a microplate comprising plural cartridge containers in which vessels are arranged in a row-wise or column-wise line in a base member thereof and a binding part formed so as to be substantially like teeth of a comb having intervals between the cartridge containers able to be inserted by partitions and binding the end of each cartridge container, wherein the partitions are arranged so as to be substantially in parallel mutually at a fixed interval on the stage where the microplate is put and are projected upward above the opening section of each vessel in order to mutually partition the cartridge containers, wherein each vessel comprises a gap part formed near a center of an inside bottom part thereof to have a smaller width and a greater length than a caliber of a front end portion of a liquid sucking/discharging line adapted to be inserted in the vessel and pulled out of the vessel, a uniformly falling slope extending from an inside wall of the vessel toward a border of the gap part, wherein the gap part is formed to have a shape being capable of aspirating and discharging all of a quantity of liquid through the front end portion even in a state that the front end portion is disposed in contact with the inside bottom part, a surface of the slope is continuously and smoothly formed from the inside wall of the vessel to the border of the gap part, in the falling direction, and the surface of the slope is free of protrusions or depressions.

* * * * *